United States Patent [19]

Duff et al.

[11] Patent Number: 5,010,005

[45] Date of Patent: Apr. 23, 1991

[54] BIO-OXIDATION OF HIGH ALCOHOLS IN NON-AQUEOUS REACTION MEDIA

[76] Inventors: Sheldon J. B. Duff, 35 Merritt Ave., Ottawa, Ontario, Canada, K1S 0J5; William D. Murray, 868 Champman Blvd., Ottawa, Ontario, Canada, K1G 1V2

[21] Appl. No.: 513,765

[22] Filed: Apr. 24, 1990

[30] Foreign Application Priority Data

Apr. 28, 1989 [CA] Canada .................................... 599191

[51] Int. Cl.[5] ........................... C12R 1/84; C12P 7/24
[52] U.S. Cl. .................... 435/147; 435/178; 435/180; 435/182; 435/190; 435/938
[58] Field of Search ............... 435/147, 938, 180, 182, 435/178, 190

[56] References Cited

U.S. PATENT DOCUMENTS 4,871,669 10/1989 Murray et al. ....................... 435/147

FOREIGN PATENT DOCUMENTS 1190875 7/1985 Canada ................................. 435/147
0090652 10/1983 European Pat. Off. ........... 435/147

*Primary Examiner*—Herbert J. Lilling
*Attorney, Agent, or Firm*—Alan A. Thomson

[57] ABSTRACT

Whole cells of methylotrophic yeasts are able to oxidize benzyl alcohol to benzaldehyde in aqueous reaction media. However, the low water solubility of the reactant and product of this bioconversion, combined with the ability of both to strongly inhibit the reaction, suggested to us the use of non-aqueous reaction fluids. Using non-aqueous systems, it was found that *Pichia pastoris* can be used to oxidize higher alcohols. The alcohol oxidase from such yeast had been previously reported unable to oxidize such alcohols. Purified alcohol oxidase was shown to function in a number of two-phase systems of varied aqueous to organic phase concentrations. The stability and biocatalyst recovery of the enzyme was improved by immobilization.

18 Claims, 3 Drawing Sheets

BIO-OXIDATION OF HIGH ALCOHOLS IN NON-AQUEOUS REACTION MEDIA

BACKGROUND AND PRIOR ART

This invention relates to a method of oxidizing long straight-chain alcohols and aromatic alcohols to their corresponding aldehyde using a methanol induced alcohol oxidase of methyltrophic yeasts in a biphasic reaction media. More specifically, this invention relates to the use of whole cells of *Pichia pastoris* in a two-phase reaction fluid to produce benzaldehyde, hexanal, heptanal, octanal, nonanal, decanal, undecanal, phenyl acetaldehyde or hydrocinnamaldehyde and, secondly to the improvements in the process which can be achieved through the use of a purified alcohol oxidase in a two phase reaction system.

Growth of some methyltrophic yeasts of the genera Pichia, Hansenula, Candida and Torulopsis on limiting amounts of methanol results in the synthesis of sub-cellular organelles known as peroxisomes. These organelles contain alcohol oxidase and catalase, two enzymes which act in concert to oxidize methanol to formaldehyde, the first step in the pathway which will ultimately result in complete degradation of methanol. When whole cells of the yeast are exposed to alcohols other than ethanol, the alcohol to aldehyde oxidation step is carried out, however, further degradation of the aldehyde is prevented by the substrate specificity of the second enzyme in the pathway, formaldehyde dehydrogenase. For this reason, the aldehyde product accumulates and the non-growing whole cells can be used as a biocatalyst in a process designed to produce a range of oxidized products. (W.D. Murray et al, Canadian Patent Application 588,365, 16 Jan. 1989.)

In the above cited Canadian patent application, whole cells of *P. pastoris* were used in an aqueous system to oxidize saturated and unsaturated straight chain and aromatic primary alcohols to their corresponding aldehydes. The rate of oxidation decreases with increasing chain length and with the addition of branches to the alcohol. Although a decrease in enzyme efficiency might be expected as one moves farther from the natural substrate of the enzyme, the problem is compounded by the decreasing water solubility of the reactants and products as the chain length increases. Particularly in reaction systems in which substrate and/or end product inhibition is severe, precipitation of either alcohol or aldehyde from solution can have extremely adverse effects on process kinetics because of the exposure to the enzyme to essentially pure inhibitor. The use of an essentially non-aqueous reaction medium in which both reactants and products are more soluble has been found to be a means, to improve the yield of the desired product.

The prior art demonstrates that methanol-induced alcohol oxidase from *P. pastoris*, or other methylotrophic yeasts, show a broad substrate specificity for short chain normal primary aliphatic alcohols. (R. Couderc and J. Baratti, Agric. Biol. Chem. 44: 2279–2289, 1980; R.N. Patel et al, Arch. Biochem and Biophys. 210: 481–488, 1981; Y. Tani et al, Agric. Biol. Chem. 36: 76–83, 1972; and U.S. Pat. No. 4,619,898.) Patel et al (op.cit.) determined that purified alcohol oxidase from *P. pastoris* was unable to oxidize secondary alcohols, diols, aromatic alcohols, cyclohexanol, tert butanol, 2-amino-ethanol or 2-amino-1-propanol. The concept of carrying out enzymatic reactions by means of the use of biphasic aqueous-organic systems is not novel. For example, Canadian Patent No. 1,005,771 discloses the use of laccase, steroid dehydrogenase lipase, lactic dehydrogenase and alcohol dehydrogenase in a biphasic system. However, based on the reports in the prior art which state that alcohol oxidase is unable to oxidize long chain alcohols, it was quite unexpected that use of a biphasic system would extend the known substrate range of alcohol oxidase to include benzyl alcohol, heptanol, octanol, nonanol, decanol, undecanol, phenethyl alcohol and 3-phenyl-1-propanol.

U.S. Pat. No. 3,880,739 discloses the oxidation of hydrophobic paraffins or alcohols to aldehydes of corresponding chain lengths by use of an aqueous suspension of a crude enzyme mixture in a hydrocarbon phase. In particular the enzymes were extracted from Pichia yeast cells which had been grown on an n-tetradecane substrate. It has recently been reported by G.D. Kemp et al (Appl. Microbiol. Biotechnol. 29: 370–374, 1988) that alkane grown *Candida tropicalis* produced an alcohol oxidase quite distinct from the alcohol oxidase previously reported for methylotrophic yeasts. The specificity of this alkane-induced enzyme for saturated primary alcohols differed from the methanol-induced enzyme. The optimum activity of the alkane-induced alcohol oxidase was towards dodecanol, with virtually no activity against the short chain ($C_2$–$C_6$) alcohols. The method disclosed in U.S. Pat. No. 3,880,739 is directed to an alkane-induced enzymes for the oxidation of long-chain alcohols. One aspect of the present invention is directed to a strain of *P. pastoris* induced by methanol to produce a different enzyme which was, prior to this invention, not known to oxidize longchain substantially water-insoluble alcohols.

SUMMARY OF THE INVENTION

According to the present invention, there is provided a method of oxidizing poorly water soluble aliphatic alcohols and aromatic alcohols to their corresponding aldehydes comprising contacting the alcohol with methanol induced methylotrophic yeast alcohol oxidase in a biphasic reaction medium.

Further according to the present invention the methylotrophic yeasts are selected from the group consisting of: yeasts occurring in the genera Pichia, Hansenula, Candida and Torulopsis; and the alcohols ar selected from the group consisting of: benzyl alcohol, hexanol, heptanol, octanol, nonanol, decanol, undecanol, phenethyl alcohol and 3-phenyl-1-propanol.

Also according to the present invention, the organic phase component is selected from the group consisting of hexane, toluene, ether, chloroform and ethylacetate and mixtures thereof.

Also according to the present invention, the alcohol oxidase is selected from the group consisting of alcohol oxidase in non-growing whole cells, purified free alcohol oxidase and purified immobilized alcohol oxidase.

DETAILED DESCRIPTION

Figure 1:
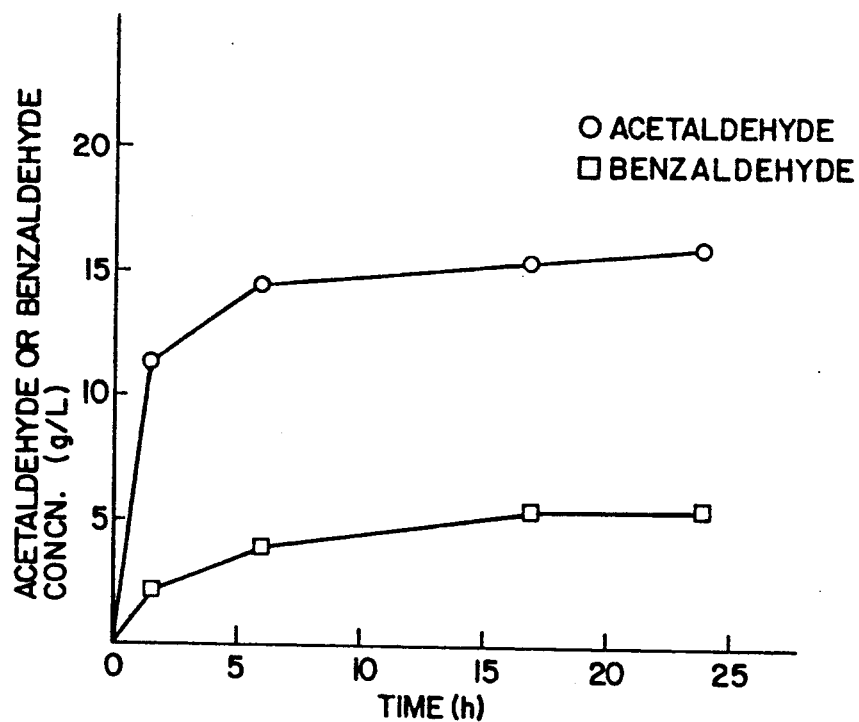
FIG. 1 shows the oxidation of ethanolO and benzyl alcohol □ by whole cells of *Pichia pastoris* in aqueous media. Biomass concentration was 3.6 g/L and initial substrate concentration was 20 g/L.

This invention relates to a method of oxidizing long straight-chain alcohols and aromatic alcohols to their corresponding aldehyde using a methanol induced alcohol oxidase of methylotrophic yeasts.

Methylotrophic yeasts of the genera Pichia, Hansenula, Candida and Torulopsis when grown on methanol synthesize an alcohol oxidase that can oxidize short chain alcohols to their corresponding aldehyde. It has been demonstrated herein that in a biphasic system the substrate specificity of methanol induced alcohol oxidase can be extended to longer straight chain alcohols and aromatic alcohols using Pichia pastoris as an example of the methylotrophic yeast. In such a biphasic reaction system, the enzyme is restricted to a small aqueous phase volume and the product is removed and concentrated in a catalyst-free organic phase. Since the methanol induced-alcohol oxidase from these various yeasts are similar, it would be obvious to those skilled in the art to expect that the enzyme from other methylotrophic yeasts could similarly oxidize these substrates in a biphasic system.

The substrates used in the present invention are, for example: $CH_3(CH_2)_nCH_2OH$ and

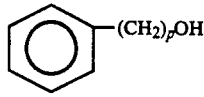

wherein $n=4-9$, and $p=1-3$. The preferred substrates being hexanol, heptanol and octanol ($n=4-6$).

Since solvent suspended alcohol oxidase is able to oxidize a number of alcohols previously reported to be inert to its activity, it should be obvious to one skilled in the art that the oxidase of the present invention may be able to oxidize other substrates such as sugars, sugar alcohols or pharmacological compounds. Such changes in enzyme activity have been widely reported for other enzymes in organic solvents.

In one aspect of the present invention the alcohols were oxidized in a biphasic system using nongrowing whole cells of P. pastoris and purified alcohol oxidase from P. pastoris, catalase and FAD, in a free and immobilized system.

In using non-growing whole cells of P. pastoris the preferred method is to suspend the cells in a 1-5% aqueous volume, and the substrate is dissolved in a 95-99% organic phase at a concentration of 5-50 g/L.

In using free purified alcohol oxidase, the alcohol oxidase is mixed with catalase in an activity ratio of about 1300 U of catalase to one unit of alcohol oxidase. The substrate is present in a 95-99% organic phase at a concentration of 5-50 g/L. The alcohol oxidase is in contact with the substrate at a concentration range of 0.05-0.75 U of enzyme/mg of substrate.

In using purified immobilized alcohol oxidase, the alcohol oxidase is immobilized on a beaded agarose gel at a concentration from about 35 mg/5 ml of gel to about 225 mg/5 ml of gel.

A number of different solvents including hexane, toluene, ether, chloroform and ethylacetate were investigated in the two phase reaction system. Mixtures of such solvents would also be operable. In general terms, the requirements of a solvent are that it be non-toxic, and be largely immiscible with an aqueous cosolvent. As well, the solvent should be chosen so that when it is in equilibrium with an aqueous component of the reaction mixture, the product is very strongly partitioned to the organic phase while the reactant is partitioned between the phases such that most of the reactant is in the organic phase while some remains in the aqueous phase for reaction. Further, the product should be easily separated from the solvent. For practical purposes, the solvent chosen should be inexpensive, available in large quantities, and sterilizable.

It should be apparent to anyone skilled in the art that besides the organic solvents disclosed herein, other non-aqueous reaction media could be used such as gases and supercritical fluids. It was found using the system of the present invention that hexane is the preferred solvent.

The volume of the aqueous phase component of the reaction fluid has a strong effect on the reaction rate. Using solvents presaturated with water, there was an increase in reaction rate with increasing concentration of aqueous phase to organic phase up to a concentration of 3-5%. Increases in the aqueous phase concentration results in an exponential increase in interfacial area. However, the positive effect of increased interfacial area is balanced by the increased potential for interfacial denaturation of the enzymes involved. The volume of the aqueous phase component also effects the inhibition of the enzyme by the product. The use of a small aqueous phase ensures that alcohol oxidase and catalase are intimately associated thereby improving biocatalyst stability and allowing sustained enzyme activity. This effect can be further enhanced through co-immobilization on a solid support resin. To others skilled in the art, other methods might be obvious by which such enforced intimacy can be brought about, i.e., co-lyophilization, co-crystallization or co-precipitation of the two enzymes.

The reaction can be carried out at temperatures from 1-45° C., however, the initial reaction rate is highest at 30° C., and therefore this temperature is preferred.

The aldehyde product can be separated from the medium by distillation, liquid/liquid extraction or any other commonly known downstream processing techniques. The reaction medium following product recovery can be recycled.

The invention is illustrated further by the following examples which, however, are not to be taken as limiting in any respect.

EXAMPLE 1

Whole Cell Oxidation of Long-chain Alcohols

Pichia pastoris was obtained from the American Type Culture Collection, Rockville, Maryland, U.S.A.

(ATCC 28485). The growth and maintenance medium consisted of: $KH_2PO_4$ 2.6 g/L; $K_2HPO_4$ 0.3 g/L; $(NH_4)_2SO_4$ 1.5 g/L; $MgSO_4 \cdot 7H_2O$ 0.3 g/L; Difco yeast extract 1.9 g/L; $FeSO_4 \cdot 7H_2O$ 1 mg/L; $CuSO_4 \cdot 5H_2O$ 5 μg/L; $H_3BO_3$ 10 μg/L; $MnSO_4 \cdot H_2O$ 10 μg/L; $ZnSO_4 \cdot 7H_2O$ 70 μg/L; $NaMoO_4 \cdot 2H_2O$ 10 μg/L. After the medium was autoclaved and cooled, methanol (10 g/L) and a vitamin solution (J.P. van der Walt and A.E. van Kerken, Antonie van Leeuwenkoek 27: 81-90, 1961) (2 mL) were added. Growth of the organism was carried out in Erlenmeyer shake flasks at 30° C. on a reciprocal shaker (200 rpm). After 72 hrs growth, biomass was harvested by centrifugation (4000 g, 5 min) washed with 0.1 M phosphate buffer pH 8, and resuspended in 0.5 M Tris buffer (pH 8).

Unless otherwise stated, the reaction conditions for whole cell systems in aqueous solution (0.5M Tris pH 8) were as follows: 25 ml of the biomass suspension was dispensed into 125 mL serum vials and the substrate was added to the concentration listed in Table 1. The final biomass concentration was 5 g/L. The vials were flushed with oxygen, capped and sealed to prevent loss of reactants or products from the system. The vials were pressurized with oxygen (15 psig) and shaken (200 rpm) at 30° C. during the reaction. A sample was withdrawn following the reaction time listed in Table 1 and centrifuged (15000 g, 1 min) to remove biomass and stop the reaction. The supernatant liquid was diluted 1:1 with internal standard for gas chromatography. In some cases, a portion of the sample was extracted with 9 volumes of warm (50° C.) water, to solubilize insoluble separated product, mixed thoroughly by vortexing, and then diluted 1:1 with internal standard before assaying by gas chromatography. In all experiments the vials were regularly repressurized with oxygen throughout the reaction period.

The method of conversion of higher alcohols using whole cells in a two-phase reaction system was as follows. One gram of *Pichia pastoris* cell paste (pellet resulting from a 10 minute, 9154 g centrifugation) was placed in a 125 ml serum vial and dispersed in 2 ml of $H_2O$ (aqueous phase).

TABLE 1

The Conversion of Higher Alcohols By Whole Cells Of *Pichia pastoris* In Aqueous and Two Phase Reaction Media

| Alcohol | Concn. (g/L) | Aldehyde | Aqueous (g/L) | 2-Phase (g/L) | Reaction Time (h) |
|---|---|---|---|---|---|
| hexanol | 30 | hexanal | 5.0 | | 12 |
| | | | | 10.6 | 6 |
| | | | | 12.4 | 24 |
| heptanol | 20 | heptanal | NC | | 24 |
| | | | | 8.3 | 6 |
| | | | | 10.3 | 24 |
| octanol | 20 | octanal | NC | | 24 |
| | | | | 5.4 | 6 |
| | | | | 9.5 | 24 |
| nonanol | 20 | nonanal | NC | | 24 |
| | | | | 0.4 | 6 |
| | | | | 0.7 | 24 |
| decanol | 20 | decanal | NC | | 24 |
| | | | | 0.7 | 24 |
| undecanol | 20 | undecanal | NC | | 72 |
| | | | | 0.4 | 72 |
| phenethyl alcohol | 10 | phenyl acetaldehyde | 0.2 | | 12 |
| | | | | 0.2 | 24 |
| 3-phenyl-1-propanol | 10 | hydrocinnam- | 0.8 | | 12 |
| | | | | 3.56 | 6 |

TABLE 1-continued

The Conversion of Higher Alcohols By Whole Cells Of *Pichia pastoris* In Aqueous and Two Phase Reaction Media

| Alcohol | Concn. (g/L) | Aldehyde | Aqueous (g/L) | 2-Phase (g/L) | Reaction Time (h) |
|---|---|---|---|---|---|
| | | aldehyde | | 5.40 | 24 |

NC = no conversion

Then 48 ml of hexane containing the substrate (concentration in Table 1) were added to form the organic phase. The reaction was conducted as described above. Samples from the organic phase were withdrawn at the indicated times (Table 1) and the concentration of aldehyde product determined by gas chromatography.

The substrates and products were assayed using a Hewlett-Packard 5790A gas chromatograph equipped with a Chromasorb 101 packed column. The carrier gas was helium and the column was run isothermally at 220° C. For aqueous reaction systems the internal standard was isopropyl alcohol (20 g/L). In non-aqueous systems octanol (20 g/L) was dissolved in the appropriate solvent and used as internal standard.

Figure 2:
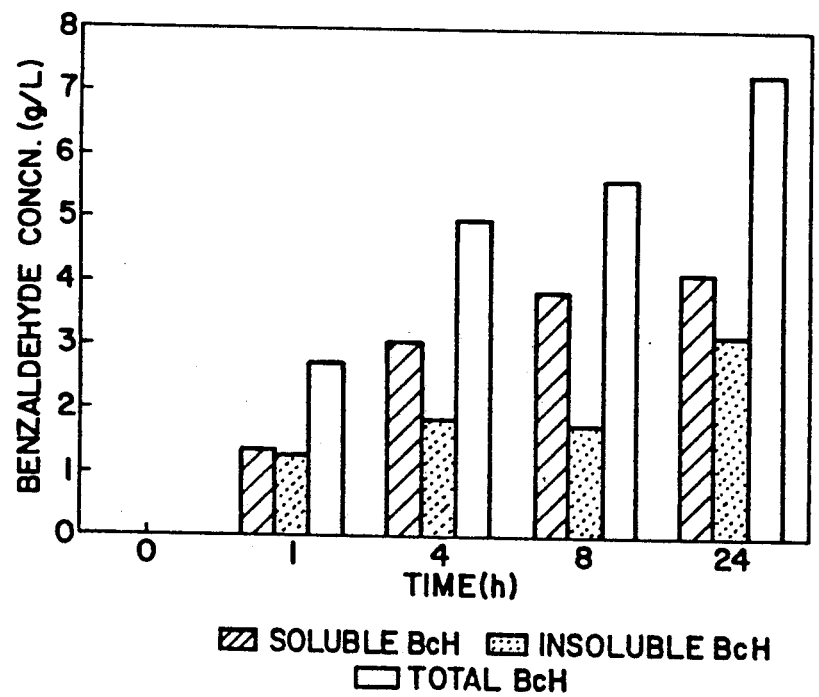
FIG. 2 demonstrates end product insolubility during batch conversion of benzyl alcohol to benzaldehyde (BcH) by whole cells of *Pichia pastoris* in aqueous reaction fluid.

The use of whole cells of *Pichia pastoris* in an aqueous reaction fluid resulted in a relatively low level of benzaldehyde production as compared to the use of the same system for the ethanol to acetaldehyde biotransformation (FIG. 1). Not to be bound by any particular theory, since benzyl alcohol is not a substrate for growth of *P. pastoris* the reduced rate of oxidation may be due in part to a restricted rate of uptake of benzyl alcohol by the whole cells. As well, benzyl alcohol is structurally very different from the natural substrate for alcohol oxidase, methanol. Aside from these inherent problems, a third difficulty is associated with the low aqueous solubility of the product of the reaction, benzaldehyde, and to a lesser degree the substrate, benzyl alcohol. The solubility of benzaldehyde in water is approximately 3 g/L. Once this level of benzaldehyde is reached in the reaction vessel, benzaldehyde begins to precipitate out of solution and the enzyme protein at the interface between the phases is exposed to droplets of pure benzaldehyde. Benzaldehyde is an extremely potent inhibitor of alcohol oxidase, and exposure of the enzyme to pure benzaldehyde results in rapid deactivation of the enzyme. To illustrate the point more clearly, a similar reaction was carried out using whole cells in aqueous reaction fluid to oxidize benzyl alcohol. In this case, however, the reaction fluid was assayed undiluted as well as after a 1:10 dilution with water. The different values obtained using these two assay techniques (FIG. 2) serve to highlight the problems owing to benzaldehyde solubility. For example, at 24 hrs of reaction time, approximately 3 g/L benzaldehyde exists in the reactor in an insoluble form. This level of benzaldehyde is sufficient to cause complete inhibition of the reaction system.

Oxidation of benzyl alcohol by whole cells in aqueous reaction fluid followed Michaelis-Menten kinetics at low substrate concentrations. At benzyl alcohol concentrations greater than 20 g/L a strong inhibition of the reaction by the substrate, benzyl alcohol is observed. At a substrate concentration of 40 g/L, the reaction rate is reduced by approximately 60% as compared to the rate at a substrate concentration of 20 g/L. At higher substrate concentrations, the aqueous solubility limit for benzyl alcohol is approached, and the problems associated with substrate inhibition are exacerbated. Kinetic analyses such as these are useful from the point of view of process design. The problems associated with substrate inhibition alone could be overcome by using a fed-batch or continuous feeding regime to maintain the level of benzyl alcohol in the reaction vessel at or near 20 g/L. However, the low water solubility of benzaldehyde and the associated strong negative effect on reaction rate is more difficult to overcome. For this reason examination of the kinetics of alcohol oxidase activity in an aqueous two-phase reaction system was carried out.

As can be seen in Table 1, except for the conversion of phenethyl alcohol to phenyl acetaldehyde, there is a significant improvement in aldehyde yields when compared to the aqueous reaction system. The methanol-induced alcohol oxidase from *P. pastoris*, as already shown in the prior art, was unable to oxidize the long-chain alcohols; for example, heptanol, octanol, nonanol, decanol and undecanol in an aqueous reaction media. However, using the two-phase reaction system of the present invention, oxidation of these alcohols was achieved.

EXAMPLE 2

Optimization of the Two-phase Reaction System Using the Oxidation of Benzyl Alcohol to Benzylaldehyde As a Model System a) Effect of organic component on oxidation of benzyl alcohol The choice of solvent has been shown to be critical to enzyme performance in two-phase systems (R.Z. Kazandjian et al, Biotechol Bioeng. 28: 417–421, 1986). In microaqueous systems the solubility of water in the solvent of interest is important in that the anhydrous solvent may strip the enzyme of bound water which is essential for its catalytic activity. This problem is easily overcome, however, by pre-saturating the solvent with water or an appropriate buffer. Only in reaction systems in which it is desirable to have an enzyme catalyse a reaction which is thermodynamically different to that catalyzed in aqueous reaction medium is an extremely low water content critical. For example, lipase, which normally catalyses hydrolyses in aqueous reaction media, can be used to synthesize esters and even peptide bonds given the choice of an appropriate organic reaction fluid (A.L. Margolin and A.M. Klibanov, JACS 109: 3802–3804, 1987). For the conversion of benzyl alcohol to benzaldehyde, no essential change in biocatalytic activity is desired and all reactions were performed in solvents saturated with water.

The partitioning of benzyl alcohol and benzaldehyde between 0.1 M phosphate buffer and each solvent used were measured as follows: benzyl alcohol (10 g/L) and benzaldehyde (10 g/L) were dissolved in each of the solvents of interest. Ten millilitres of each solvent were then dispensed into a test tube containing 10 ml of 0.1 M phosphate buffer (pH 8). The tubes were capped, vortexed, and the mixture was allowed to equilibrate for 1 hr at 30° C. Both phases were then assayed for benzaldehyde and benzyl alcohol as described above. Partition coefficients were expressed as the ratio of the concentration of the solute of interest in the aqueous phase: the concentration of the same compound in the organic phase.

To determine reaction rates, benzyl alcohol was presolubilized in the solvent of interest to a final concentration of 20 g/L unless otherwise specified. Alcohol oxidase and catalase were premixed in an activity ratio of 1300 U catalase activity per unit of alcohol oxidase activity. In some cases the enzyme mixture was diluted with 0.1 M phosphate buffer (pH 8) to determine the effect of changes in phase volume ratio. The enzyme mixture was then added to the solvent-substrate reaction fluid in a 125 mL serum vial. Reaction conditions were otherwise identical to those described above.

The purified alcohol oxidase was obtained from Provesta Corp. (Bartlesville, Oklahoma) and consisted of a concentrated (35 g/L) protein solution with a specific activity of 14.7 International Enzyme Units (IEU) per milligram of protein. One IEU is defined as the amount of enzyme which will oxidize one micomole of ethanol to acetaldehyde per minute at pH 7.5 at 25° C. The enzyme was stored frozen (−20° C.) until used. Beef liver catalase was obtained from Boehringer Mannheim Inc. as a 20 g/L suspension with a specific activity of 65000 U/mg. It was stored at 4° C.

As shown in Table 2 the rate of benzaldehyde production was highest in systems which contained hexane as the reaction fluid. The varied activity of alcohol oxidase in different organic solvents arises mainly from the partitioning of benzyl alcohol between the solvent and the aqueous phase. Benzaldehyde is more soluble in all of the solvents tested than in phosphate buffer, however, only in the hexane system is a partitioning of the benzyl alcohol into the aqueous phase favoured. Provided that the substrate is present at levels which do not inhibit alcohol oxidase, the substrate is partitioned into the aqueous phase where it can be acted upon by the biocatalyst. The product is partitioned into the organic phase, thereby lessening end product inhibition and aiding product recovery.

TABLE 2

Effect of reaction fluid on conversion of benzyl alcohol to benzaldehyde in aqueous two phase systems

| Reaction Fluid | Partition Coefficient ($C_{org}/C_{aq}$) | | Reaction Rate (g/L h) | Relative Reaction Rate |
|---|---|---|---|---|
| | Benzaldehyde | Benzyl alcohol | | |
| Hexane | 15.4 | 0.37 | 2.08 | 1.0 |
| Toluene | 100 | 3.04 | 1.01 | 0.49 |
| Ether | 69.4 | 11.7 | 0.39 | 0.19 |
| Chloroform | ND | 7.81 | 0.07 | 0.03 |
| Ethylacetate | 62.0 | 15.3 | 0.09 | 0.04 |

ND indicates that benzaldehyde was not detected in the aqueous phase.

Figure 3:
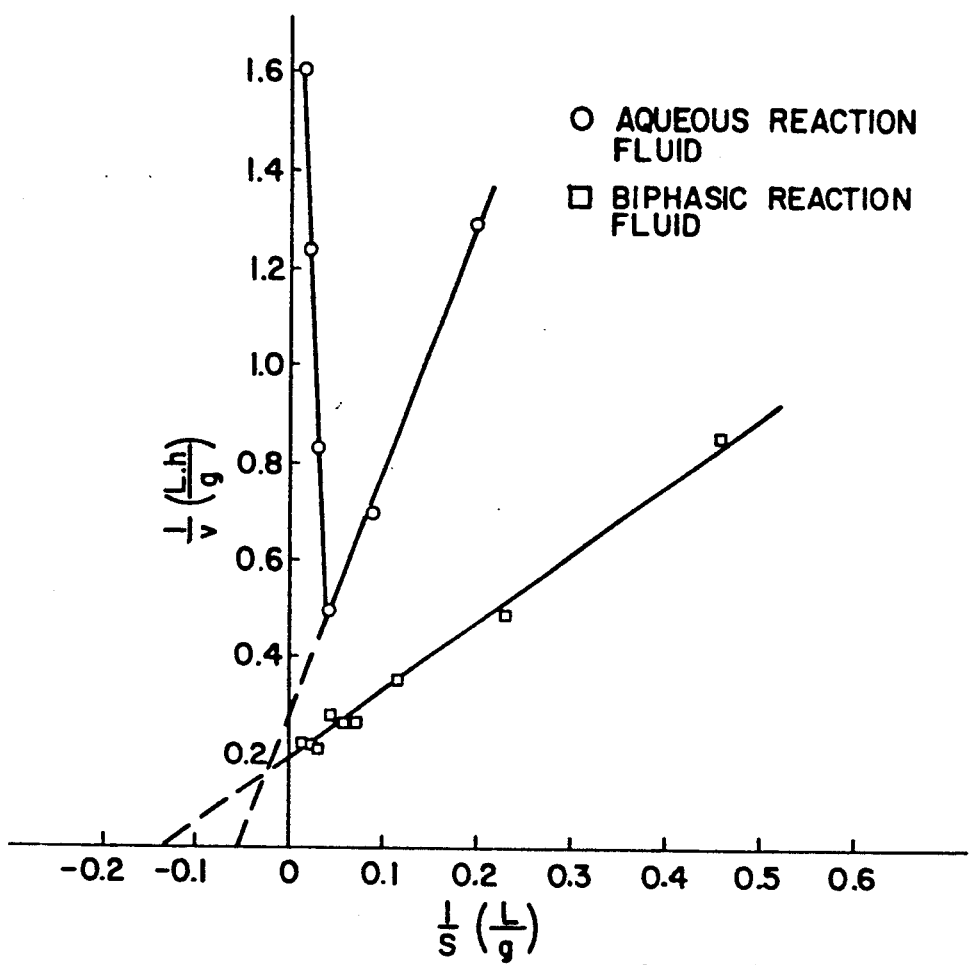
FIG. 3 shows the influence of substrate (benzyl alcohol) concentration on the rate of conversion of benzyl alcohol to benzaldehyde by whole cells of P. pastoris in an aqueous reaction fluid ○ and by purified alcohol oxidase in hexane containing 3% v/v aqueous component □.

The use of hexane as the major component of the reaction fluid has a dramatic effect on the kinetics of oxidation of benzyl alcohol (FIG. 3, Table 3). In the hexane system, some flattening of the rate curve does occur at high (>30 g/L) concentrations of benzyl alcohol. However, the very sharp decrease in rate at high substrate concentrations which was observed in the aqueous system is overcome through advantageous partitioning of benzyl alcohol between the phases. In the two phase system, optimum reaction rates (85% of $V_{max}$) could be maintained at substrate concentrations up to 54 g/L.

b) Effect of aqueous phase volume on reaction rate

Benzyl alcohol to benzaldehyde conversion was described in part a) except the percent aqueous phase was varied between 1 and 5%.

TABLE 3

Effect of enzyme loading on benzaldehyde production in two phase reaction system. Reactions which produced benzaldehyde concentrations greater than 20 g/L were operated with fed-batch addition of benzyl alcohol.

| Enzyme concentration | | Initial rate of benzaldehyde production | Cumulative benzaldehyde production | |
|---|---|---|---|---|
| (U/mL) | (g/L) | (g/L h) | Concn. (g/L) | Time (h) |
| 1.0 | 0.06 | 1.4 | 2.1 | 2.0 |
|  |  |  | 2.8 | 4.0 |
|  |  |  | 17 | 8.0 |
| 2.5 | 0.16 | 3.4 | 5.1 | 2.0 |
|  |  |  | 6.3 | 4.0 |
| 5.0 | 0.31 | 6.3 | 9.9 | 2.0 |
|  |  |  | 13 | 4.0 |
| 7.5 | 0.47 | 8.6 | 13 | 2.0 |
|  |  |  | 19 | 4.0 |
| 10 | 0.63 | 10.3 | 15 | 2.0 |
|  |  |  | 22 | 4.0 |
| 15 | 0.94 | 11.7 | 17 | 2.0 |
|  |  |  | 32 | 4.0 |
|  |  |  | 45 | 8.0 |

Figure 4:
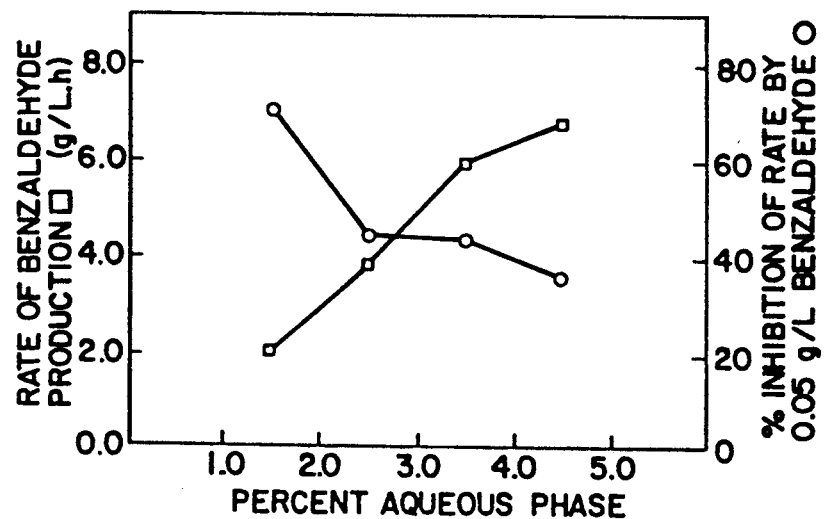
FIG. 4 shows the influence of aqueous to organic phase ratio on the rate of conversion of benzyl alcohol to benzaldehyde □ and on the degree of inhibition of the reaction by a fixed concentration of ○.

The volume of the aqueous phase component of the reaction fluid had a strong effect on the reaction rate (FIG. 4). Using solvents presaturated with water there was an increase in reaction rate with increasing volumetric concentration of aqueous phase to organic phase up to a concentration of 3-5%. Further increases in the aqueous phase component did not result in further increases in reaction rate. Increases in the aqueous phase concentration results in an exponential increase in interfacial area. At aqueous to organic phase concentration of greater than 2-3%, water in oil emulsions were formed resulting in an exponential increase in the interfacial area between the phases. Since oxygen is much more soluble in the organic phase than in aqueous solutions, oxygen transfer between the phases is facilitated by the increase in interfacial area. In addition, mass transfer of benzyl alcohol and benzaldehyde between aqueous and organic phases is enhanced by the larger interfacial area. Benzaldehyde produced in the aqueous phase through action of the alcohol oxidase and catalase is more efficiently stripped into the solvent phase. As the concentration of benzyl alcohol in the aqueous phase is depleted, an equilibrium between the amount of benzyl alcohol in each of the phases is more rapidly established in systems with larger interfacial surface areas. Thus it is possible, to some extent, to limit the negative effects associated with excessive amounts of substrate or product through physical changes to the reaction system. The positive effect of increased interfacial area is balanced by the increased potential for interfacial denaturation of the enzymes involved. In agitated reaction vessels, the phase interface is continuously recharged with new solutes. Over time, in reaction fluids with large interfacial areas, much of the enzyme protein is exposed to denaturing forces at the interface.

c) Inhibition of alcohol oxidase by benzaldehyde.

Alcohol oxidase is very strongly inhibited by benzaldehyde (FIG. 4). Similar potent inhibition of yeast alcohol dehydrogenase by aliphatic and aromatic aldehydes including benzaldehyde has been reported (W.R. Bowen et al, J. Chem. Tech. Biotechnol. 36: 191-196, 1986). In two phase systems, the degree to which alcohol oxidase is inhibited by benzaldehyde is controlled by the concentration of the inhibitor, the concentration of the enzyme, the solvent chosen as a reaction fluid, and on the volumetric ratio of the two phases present.

The effect of the first two factors is obvious, however the latter two parameters play an important role in determining the effective concentration of the inhibitor; that concentration to which the biocatalyst is exposed, potentially causing inhibition. Benzaldehyde partitions differently between the two phases depending on the solvent chosen. For example, using toluene as an extractant benzaldehyde was efficiently stripped from the aqueous phase (Table 2) and was, therefore, less able to inhibit alcohol oxidase. It is possible that this would result in improved yields over extended reaction times, despite the sacrifice in terms of initial reaction rate.

d) Immobilization of alcohol oxidase

Figure 5:
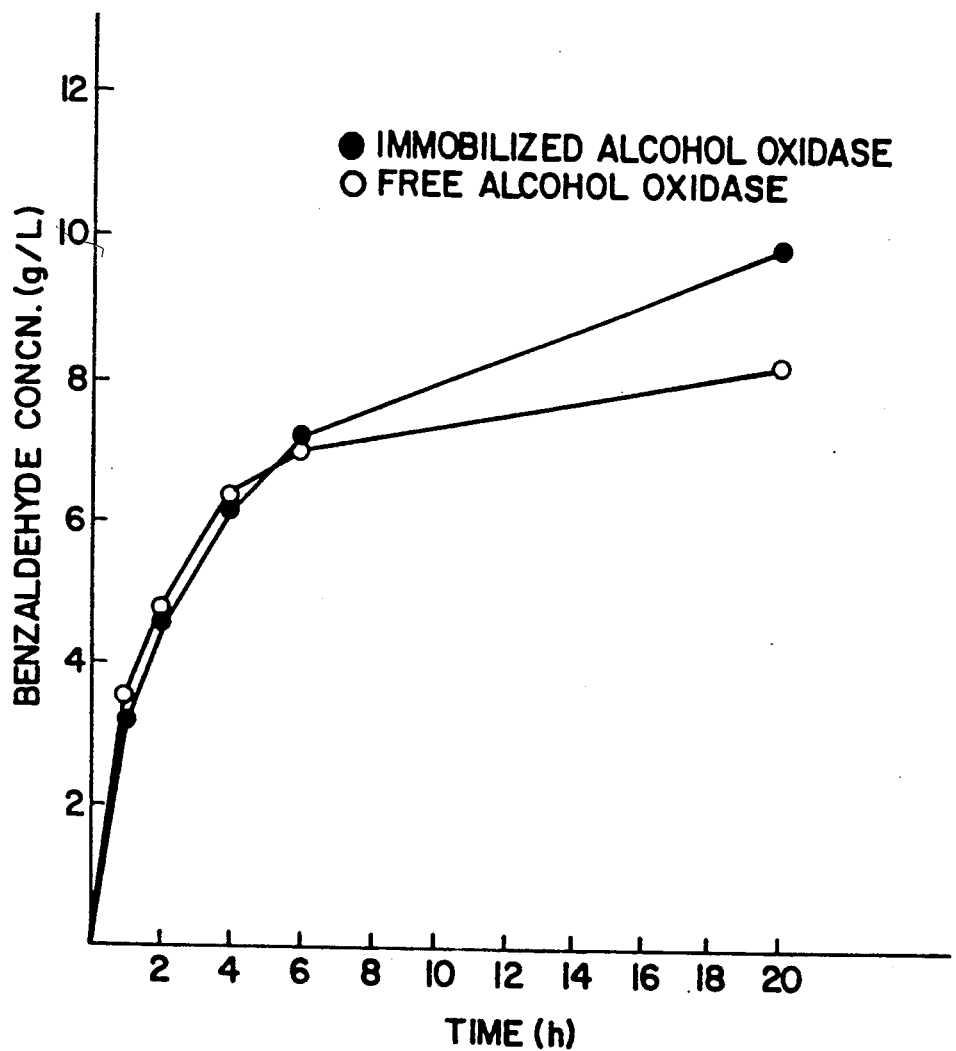
FIG. 5 depicts the time course for benzaldehyde production using free ○ and DEAE Biogel-immobilized ● alcohol oxidase. Enzyme concentration was 2.5 U/mL and the aqueous to organic phase concentration was 5%.

Alcohol oxidase was immobilized on DEAE-Biogel A TM (Bio-Rad Laboratories, CA, USA), a beaded agarose gel containing diethylaminoethyl (DEAE) anion exchange groups. The gel was equilibrated with 20 volumes of 0.01 M phosphate buffer (pH 8). Alcohol oxidase was applied to the gel (35 mg alcohol oxidase per 5 mL gel) and the gel was eluted with eight bed volumes of 0.01 M phosphate buffer (pH 8). The eluent was collected in 2 mL fractions. The protein content of the fractions was determined spectrophotometrically by measuring the absorbance of each fraction at 280 nM and comparing the values obtained with a standard curve constructed using alcohol oxidase protein. Following the column washes it was determined that 99% of the protein which was, added to the gel was retained. The gel-immobilized alcohol oxidase retained 90% of its activity as measured by initial rate. Over extended reaction times (20 h) the immobilized enzyme produced 18% more benzaldehyde than did an equivalent amount of soluble alcohol oxidase (FIG. 5). The increased stability of the immobilized enzyme was most likely due to an increase in resistance to end-product inhibition by benzaldehyde.

In previous work with DEAE-cellulose immobilized alcohol oxidase, short enzyme half-lives were attributed to desorption from the support matrix. In our work, the half life of the immobilized enzyme was not shorter than the soluble controls. Neither was there any observed desorption of alcohol oxidase from the DEAE-Biogel, however in the two-phase system such desorption would be less likely to occur because the presence of the organic phase would tend to confine the enzyme to the hydrophilic support matrix. In this system, enzyme deactivation is most likely a result of the strong inhibition affected by benzaldehyde on alcohol oxidase. Inhibition of the reaction system by hydrogen peroxide may also be a contributing factor. For both reactions catalysed by both free and immobilized enzymes, control reactors with no added catalase produced no detectable benzaldehyde. Although the addition of soluble beef liver catalase to the reaction vessels alleviated the peroxide-induced inhibition to a large extent, intimate association between the two enzymes such as exists in peroxisomes is necessary for efficient removal of the peroxide formed. For this reason, co-immobilization of catalase on the support matrix could provide, in the immobilized enzyme reactors, an environment in which peroxide is more efficiently degraded. This would also contribute to the enhanced longevity of the immobilized enzyme activity.

EXAMPLE 3

Bioxidation of Hexanol to Hexanal by P. pastoris

The conversion of hexanol was studied in several two-phase aqueous (5% v/v)/organic systems. The partition coefficients were determined as in Example 2 but expressed as solute (g/L) in organic phase/solute (g/L) in aqueous phase (see Table 4).

TABLE 4

Partition coefficients and the effect of organic solvents on the bio-oxidation of hexanol to hexanal

| Organic solvent | Partition coefficient[a] | | Hexanal produced[b] (g/L) |
|---|---|---|---|
| | Hexanol | Hexanal | |
| Hexane | 3.7 | 3.4 | 8.7 |
| Ethyl acetate | C[c] | 27.2 | 2.4 |
| Chloroform | C | C | 1.0 |
| Ether | 42.0 | 24.5 | 2.7 |
| Toluene | 15.0 | 9.8 | 2.4 |

[a]Solute (g/L) in organic phase/solute (g/L) in aqueous phase
[b]Aqueous phase (5% v/v); 24 h incubation
[c]Complete partitioning of the solute in the organic phase.

The partition coefficients of hexanol and hexanal in all of the two-phase systems tested were greater than unity, thus showing the preferential solubility of these two compounds in the organic phase. In each of these two-phase systems hexanol was successfully oxidized to hexanal by P. pastoris; however, the largest amount of hexanal was produced when hexane was used as the organic solvent (Table 4). In this water-hexane two-phase system hexanol concentrations up to 10 g/L were completely oxidized.

We claim:

1. A method of oxidizing poorly water soluble aliphatic alcohols and aromatic alcohols to their corresponding aldehydes comprising contacting the alcohol with methanol-induced methylotrophic yeast alcohol oxidase in a biphasic reaction medium which comprises an organic phase component and an aqueous phase component such that the alcohol is partitioned between the phases and the aldehyde is partitioned in the organic phase, the volume of aqueous phase being small relative to the volume of organic phase.

2. The method of claim 1 wherein the alcohols are selected from the group consisting of: $CH_3(CH_2)_nCH_2OH$ and

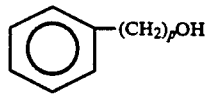

wherein n=4-9, and p=1-3.

3. The method of claim 2 wherein the alcohols are selected from the group consisting of: benzyl alcohol, hexanol, heptanol, octanol, nonanol, decanol, undecanol, phenyl alcohol and 3-phenyl-1-propanol.

4. The method of claim 1 wherein the methylotrophic yeasts are selected from the group consisting of yeast species from the genera Pichia, Hansenula, Candida and Torulopsis.

5. The method of claim 4 wherein the species of the genera Pichia is P. pastoris.

6. The method of claim 5 wherein the P. pastoris is ATCC 28485.

7. The method of claim 1 wherein the aldehyde product is separated from the medium by distillation, or a liquid/liquid extraction, and the medium recycled.

8. The method of claim 1 wherein the organic phase component is selected from the group consisting of: hexane, toluene, ether, chloroform and ethylacetate.

9. The method of claim 8 wherein the organic phase component is hexane.

10. The method of claim 1 wherein the aqueous phase component is selected from water or an alkaline buffer solution (pH 7-9).

11. The method of claim 1 wherein the percent of aqueous phase in the biphasic reaction media is about 1-5%.

12. The method of claim 11 wherein the percent of aqueous phase is about 3-5%.

13. The method of claim 1 wherein the alcohol oxidase is selected from the group consisting of: alcohol oxidase in non-growing whole cells, purified free alcohol oxidase and purified immobilized alcohol oxidase.

14. The method of claim 13 wherein in oxidation using whole cells, the cells are suspended in a 1-5% aqueous volume, and the substrate is dissolved in a 95-99% organic phase concentration of 5-50 g/L.

15. The method of claim 13 wherein, in the oxidation using purified free alcohol oxidase, the alcohol oxidase is mixed with catalase in an activity ratio of about 1300 U of catalase to one unit of alcohol oxidase.

16. The method of claim 15 wherein the alcohol oxidase is contacted with the substrate at a concentration range of about 0.05 U of enzyme/mg of substrate to 0.75 U/mg.

17. The method of claim 15 wherein the concentration of substrate ranges from about 5 g/L to 50 g/L.

18. The method of claim 13 wherein in the oxidation using purified immobilized alcohol oxidase, the alcohol oxidase was immobilized on a beaded agarose gel containing diethylaminoethyl anion exchange group at a concentration from about 35 mg/5 mL of gel to about 225 mg/5 mL.

* * * * *